(12) United States Patent
Soutorine et al.

(10) Patent No.: US 7,481,764 B2
(45) Date of Patent: Jan. 27, 2009

(54) SELF-ADVANCING DEVICE

(75) Inventors: Mikhail Soutorine, Elsternwick (AU); Nurbey Gulia, Moscow (RU); Igor Tchepikov, Elsternwick (AU)

(73) Assignee: Endogene Pty Ltd., Victoria (AU)

( * ) Notice: Subject to any disclaimer, the term of this patent is extended or adjusted under 35 U.S.C. 154(b) by 326 days.

(21) Appl. No.: 10/499,426

(22) PCT Filed: Dec. 20, 2002

(86) PCT No.: PCT/AU02/01733

§ 371 (c)(1),
(2), (4) Date: Sep. 13, 2004

(87) PCT Pub. No.: WO03/053225

PCT Pub. Date: Jul. 3, 2003

(65) Prior Publication Data

US 2005/0165278 A1    Jul. 28, 2005

(30) Foreign Application Priority Data

Dec. 20, 2001 (AU) ................................. PR9678
Feb. 21, 2002 (AU) ................................. PS0647
Apr. 8, 2002 (AU) ................................. PS1610

(51) Int. Cl.
*A61B 1/00* (2006.01)

(52) U.S. Cl. .................. 600/114; 600/141; 600/158; 604/38; 604/95.01; 604/95.02; 604/95.03; 604/95.05; 227/19; 173/152; 173/201; 173/206; 173/212

(58) Field of Classification Search ............... 600/114, 600/141, 158, 104; 604/95.01–95.05; 173/212, 173/206, 201, 152; 227/19
See application file for complete search history.

(56) References Cited

U.S. PATENT DOCUMENTS

| | | | |
|---|---|---|---|
| 3,602,102 A * | 8/1971 | Fenari ........................ 91/438 |
| 3,895,637 A | 7/1975 | Choy | |
| 4,475,902 A | 10/1984 | Schubert | |
| 5,562,601 A * | 10/1996 | Takada ........................ 600/114 |
| 5,816,342 A | 10/1998 | Prater, Jr. et al. | |
| 6,162,171 A | 12/2000 | Ng et al. | |
| 6,332,865 B1 * | 12/2001 | Borody et al. ........... 600/114 |
| 6,702,734 B2 * | 3/2004 | Kim et al. ................. 600/114 |
| 2002/0111535 A1 | 8/2002 | Kim et al. | |

FOREIGN PATENT DOCUMENTS

| WO | WO 91/12987 | 9/1991 |
| WO | WO 99/34726 A1 | 7/1999 |
| WO | WO 99/60917 | 12/1999 |

OTHER PUBLICATIONS

International Search Report for EP/02784926 dated Mar. 2, 2007.

* cited by examiner

*Primary Examiner*—Linda C Dvorak
*Assistant Examiner*—Matthew J Kasztejna

(57) ABSTRACT

A device (1) which includes an elongate body (2) with a movable mass (3) arranged for sliding movement within the body (2), the element (4) being arranged to decelerate toward an end of the body (2) in order to impart forward movement thereto, via momentum transfer, and being arranged to accelerate away from said end in order to further drive the body (2) forward, again using momentum transfer.

15 Claims, 5 Drawing Sheets

SELF-ADVANCING DEVICE

FIELD

The invention relates to a self-advancing device particularly, but not exclusively, for use in the field of medical instrumentation.

BACKGROUND

A number of self-advancing mechanisms are used in the medical industry to advance instruments, such as an endoscope, internally of a patient's body.

Self-advancing endoscopes are disclosed in, for example, U.S. Pat. Nos. 4,934,786, 5,345,925 and 5,562,601. The devices disclosed in these patents all rely on the outer surface of the endoscope having a relatively movable portion that grips the internal wall of a passage through which the endoscope is passing. In that manner, the endoscopes rely on external pushing as their source of forward motion and the resultant construction of the mechanisms to achieve that motion can be relatively complex.

Another endoscope is disclosed in International Application No. PCT/AU99/00005, which is propelled forwardly by a piston slidably mounted within a tubular member of the endoscope. The piston is caused to move toward and impact on a distal end wall of the endoscope to provide forward motion. A wire or other mechanism is used to retract the piston for subsequent acceleration and impact with the end wall, in order to further advance the endoscope. A disadvantage of such an arrangement is that the impact of the piston can produce an uncomfortable sensation within the patient and the use of a retracting wire may complicate construction of the endoscope and compromise operating efficiency, such as due to frictional resistance between the tubular member and the wire.

OBJECT

The present invention seeks to provide a self-advancing device which addresses the above disadvantages.

SUMMARY

One or more embodiments provide for a device which includes an elongate body with a movable mass arranged for sliding movement within the body. The moveable mass may be arranged to decelerate toward an end of the body in order to impart forward movement thereto, via momentum transfer. The moveable mass may further be arranged to accelerate away from the end in order to further drive the body forward also using momentum transfer. The device may also define a first flow path for applying pressurised fluid to a rear of the moveable mass and a second flow path for allowing the fluid to be discharged from between a front of the moveable mass and the end of the body. Fluid flow along the second flow path may be reduced as the moveable mass approaches the end of the body, in order to provide a fluid cushion to dampen impact between the moveable mass and the body. A third flow path is provided to inject fluid between the moveable mass and the end of the body, in order to accelerate the moveable mass in a rearward direction relative to the end of the body.

In further embodiments, a method of generating movement in the above-described device is provided. The method includes including rapidly decelerating the moveable mass toward an end of the body to impart forward movement thereto, via momentum transfer and accelerating the moveable mass away from said end in order to further drive the body forward, again using momentum transfer, by injecting fluid between the moveable mass and the end of the body.

BRIEF DESCRIPTION OF THE DRAWINGS

The invention is described, by way of non-limiting example only, with reference to the accompanying drawings, in which.

DETAILED DESCRIPTION

Figure 1:
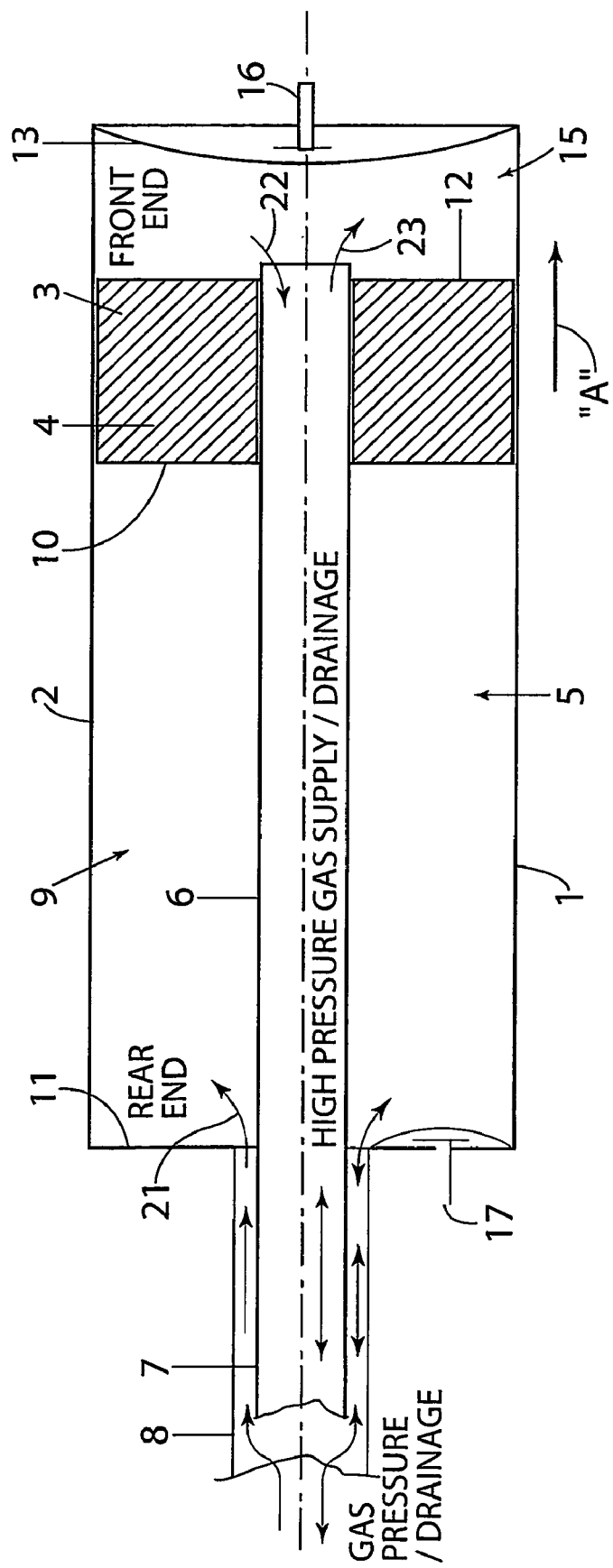
FIG. 1 is a diagrammatic cross section of a self-advancing device.

A self-advancing device 1 is shown in FIG. 1 as including an elongate body 2 with a movable mass 3, in the form of piston element 4 arranged for sliding movement along a channel 5 formed within a body 2. The body 2 is mounted on an axially extending conduit 6, which projects into the body 2 from a pipe 7. A second coaxial pipe 8 is also provided for fluid communication with a first region 9 of the channel 5, between a rear end 10 of the element 4 and a rear end 11 of the body 2. The pipe 7 maintains fluid communication with a second region 15, between a front end 12 of the element 4 and a front end 13 of the tube. Sensors 16 and 17 are also provided to detect proximity of the element relative to either end 11 or 13 of the body 2. The sensors 16,17 are shown for illustrative purposes only and they need not be in the locations shown. Indeed, the sensors may be dispensed with entirely provided the position of the element 4 within the body 2 is known or can at least be appropriately determined by some other appropriate means.

In operation, a first flow path 21 is established to force fluid into the first region 9 between the rear end 11 of the body 2 and the element 4, to drive the element 4 toward the front end 13 of the body 2. At the same time, a second flow path 22 is established to drain fluid from the second region 15, between the front end 12 of the element 4 and the end 13 of the body 2. In that manner, the element 4 may be accelerated toward the front end 13 of the body 2. Relative inertia between the element 4 and the body 2 maintains the device 1 in place up until the element 4 is adjacent the end 13 of the body 2, as determined by sensor 16, at which time, the element 4 is rapidly decelerated. The change in momentum is transferred to the body 2 so as to overcome the relative inertia of the body 2 and impart forward motion thereto. The deceleration is effected in such a manner that the fluid in the second region, between the front end 12 of the element 4 and the body 2 acts to dampen an impact between the element 4 and the body 2 itself. The dampening effect may be achieved by regulating the fluid flow along the second flow path 22.

A second working cycle is then implemented, in which the element 4 is rapidly accelerated away from the front end 13 of the body 2 by injecting high-pressure fluid along a flow path 23 through the conduit 6 and into the second region 15, between the front end 13 of the element 4 and the body 2, so that the inertia of the body is again overcome, to allow the body 2 to again move in a forwardly direction, indicated by arrow "A". The element 4 is then decelerated and brought to a stop, once it is proximate to the rear end 10 of the body 2, as detected by sensor 17, so as to position the element 4 for commencement for another working cycle.

The specific construction of the device, which allows flow paths 21,22,23 to be defined, as well as the dynamic regulation of fluid flow along those flow paths, constitutes an overall control means which provides for control of the fluid flow between the element 4 and the body 2 to thereby effect the frequency and rate of deceleration or acceleration, as required, in order to move the device. The control means may also be used to cause reverse motion of the device by essentially reversing the direction of the working cycles.

Figure 2:
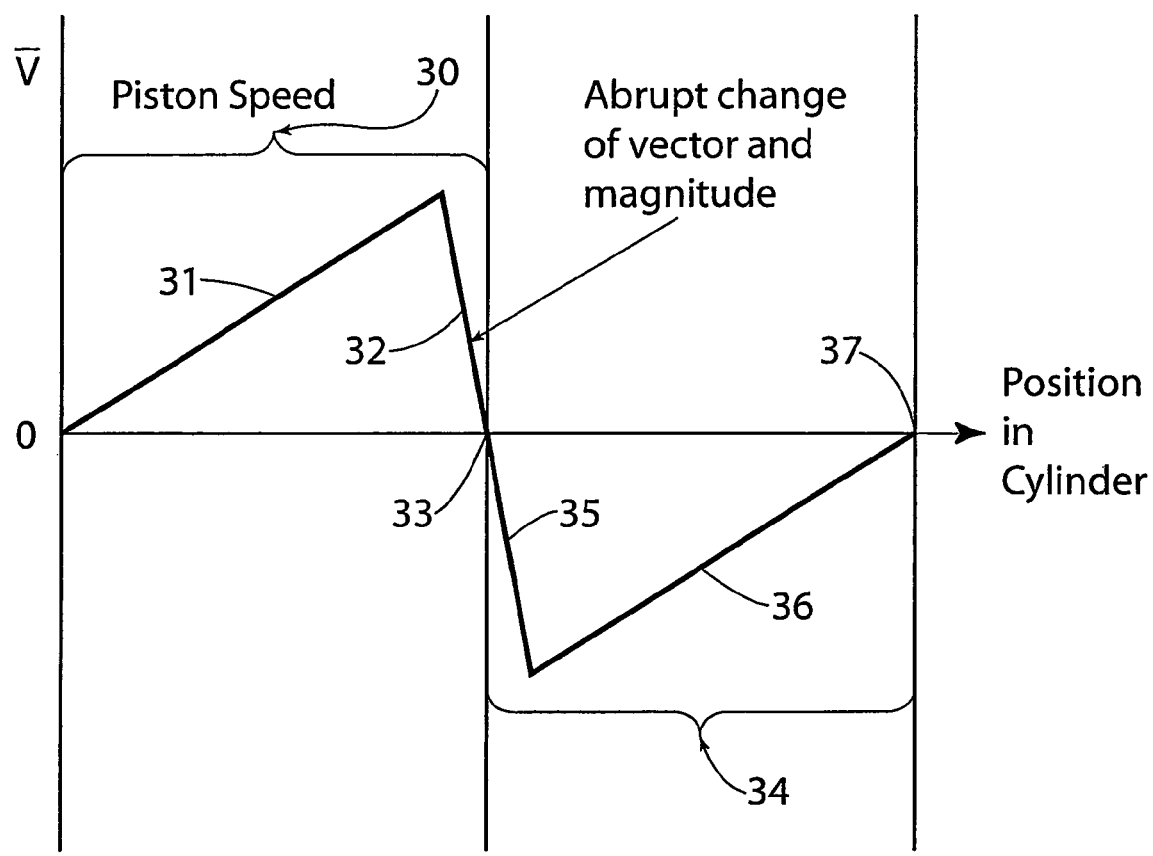
FIG. 2 is a graph, illustrating velocity of a piston element of the device of FIG. 1.

A more specific example of the working cycles is described with reference to FIG. 2. The first described working cycle is indicated by reference numeral 30 and comprises a first phase 31 where the element 4 is accelerated along the channel 5 and a second phase 32 where the element is rapidly decelerated to a rest position, indicated by reference numeral 33, which corresponds to the element 4 being adjacent the front end 13. The second work cycle 34 then includes an identical and reversed initial phase 35 of rapid acceleration followed by a deceleration phase 36 which continues until the element 4 is again at a rest position indicated by reference numeral 37, adjacent the rear end 11 of the body 2.

Figure 3:
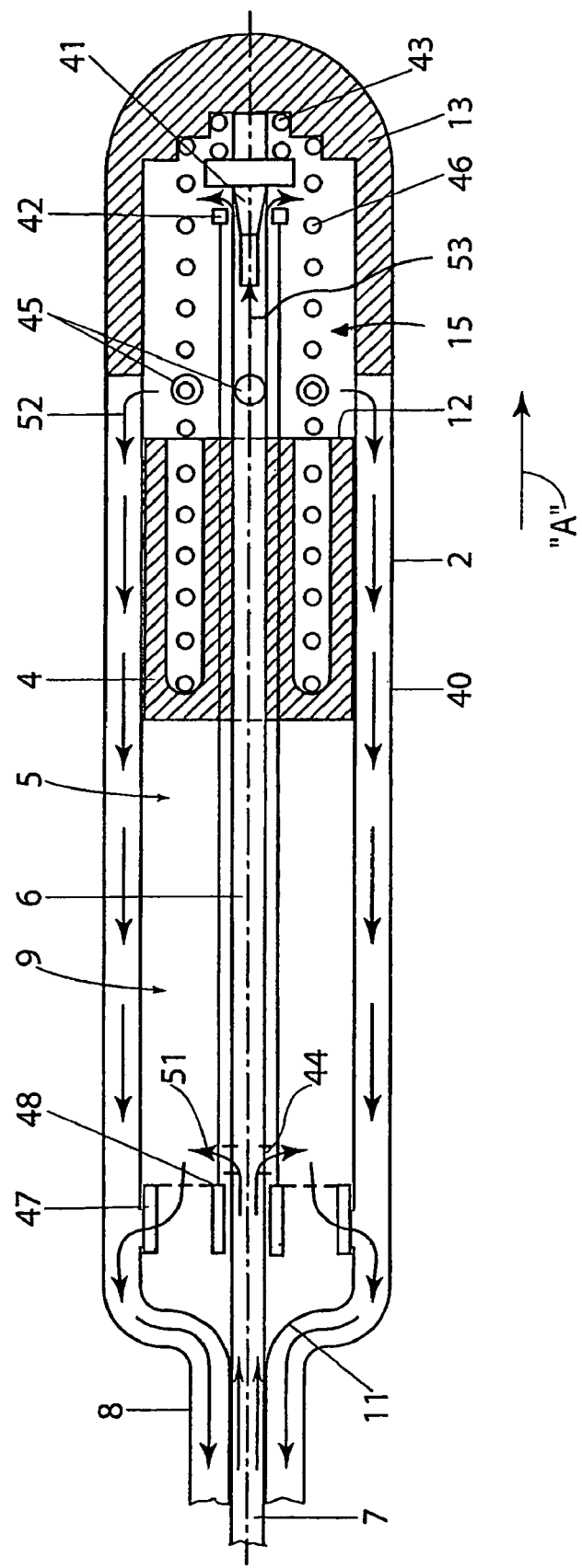
FIG. 3 is a cross-sectional view of an alternative form of self-advancing device.

Referring now to FIG. 3, a device 40, similar to device 1, is shown and like reference numerals are used to denote like parts. The device 40 operates in substantially the same manner insofar as relative acceleration and deceleration of the element 4 is used to impart motive drive to the body 2. As with FIG. 1, the device 40 includes an elongate body 2 with a piston element 4 mounted on a conduit 6 for sliding motion in a channel 5 arranged internally of the body 2. The conduit 6 includes a main valve 41 at a forward end 42 thereof. The valve 41 is biased into a closed position, by the action of a spring 43 which is provided between the valve 41 and a front end 13 of the body 2. Under that condition, positive fluid pressure is applied to the conduit 6, from a pipe 7 coupled thereto such that fluid is forced along a first flow path 51, through secondary valves 44 and into a first region 9, between a rear end 11 of the body 2 and the element 4, so as to force the element 4 toward the front end 13 of the body 2. As the element 4 passes through the channel 6, fluid is forced out of a second region 15, between a front end 12 of the element 4, through openings 45, along a second flow path 52 which passes down a return passage 46 formed in the body, for communication with a second coaxial pipe 8. Progression of the element 4 in a forwardly direction, indicated by arrow "A" results in the openings 45 being closed and the second flow path 52 being interrupted. Positive fluid pressure, however, maintains the forward motion of the element 4 although such motion is rapidly decelerated by action of fluid within the second region 15 as well as compression of a spring 46, so that the element 4 is brought to standstill. Immediately prior to that position, the valve is caused to open by engagement with the element 4 and a third flow path 53 is then established by virtue of positive pressure forcing fluid through the valve 41 and thereby causing rapid acceleration of the element 4 in a reverse direction. Under that condition, the first flow path 51, where fluid entered the first region 9, is closed off and the fluid remaining in the region 9 between the element 4 and the rear end 11 of the body 2 is caused to exit via further valves 47. In addition, once the element 4 moves past the openings 45, fluid from the third flow path 53 exits via those openings 45 and the element 4 decelerates and is pushed back at a reduced rate, by action of the spring 46.

As the element 4 approaches the rear end 11 of the body 2, additional valves 48 are contacted and forced open to allow for egress of any remaining fluid in the region 9 between the rear 11 of the body 2 and a rear 10 of the element 4. The valves 44 are subsequently opened and the first fluid flow path 51 is again established to accelerate the element 4 toward the front end 13 of the body 2.

Figure 4:
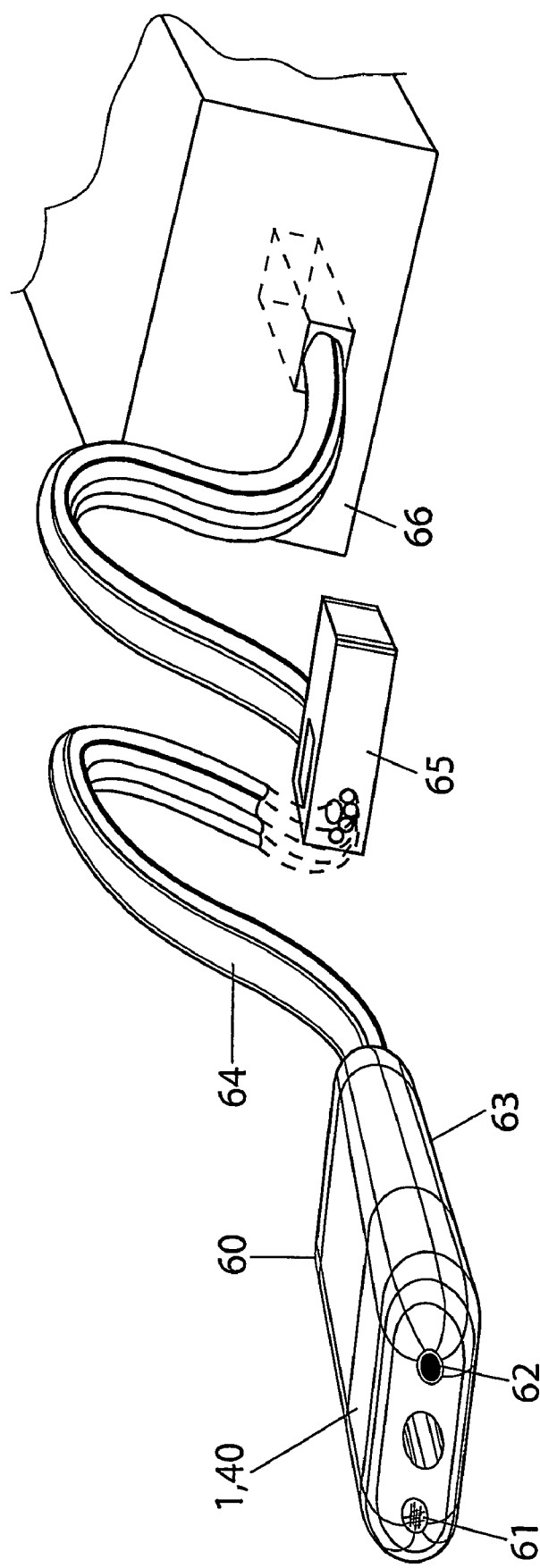
FIG. 4 is a perspective view of a self-advancing endoscope.

The above described self-advancing device 1,40 may be used to propel any suitable probe or the like and, in particular, the device may be fitted to an endoscope 60, such as shown in FIG. 4. In that arrangement, the device 1,40 may additionally include a light source 61 and a camera 62, as well as suitable location means 63 for securing the endoscope in a chosen location. The endoscope 60 may include a cable 64 which houses the pipes 7,8 to facilitate operation of the control means, including provision of energy, air, water and any other required consumerables. The cable 64 may be integrally formed with the device 1,40 and be adapted for a single-use type application, where it can be detachably secured to a junction box 65 which is provided between the endoscope 60 and a reusable controlling unit 66.

Figure 5:
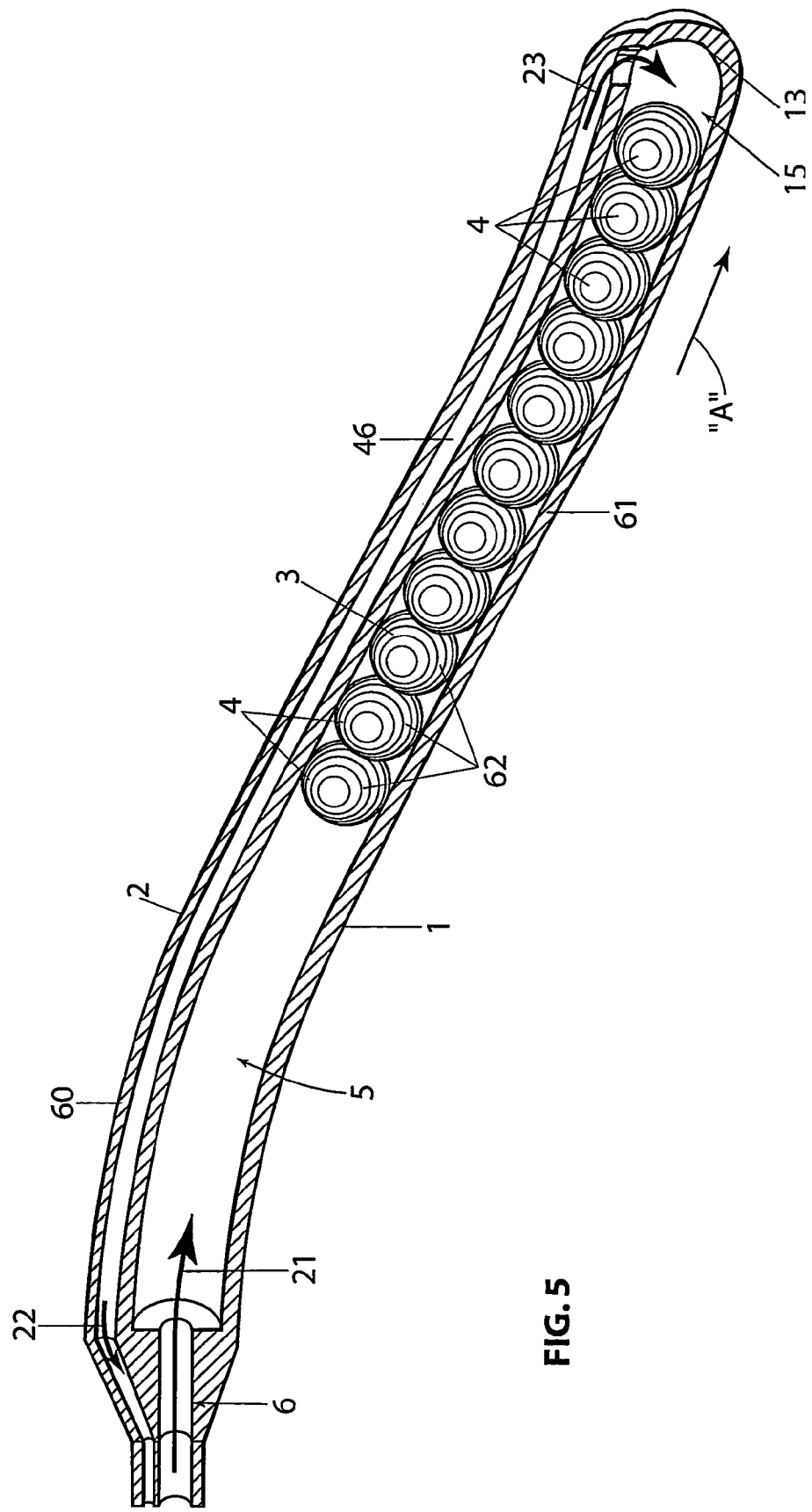
FIG. 5 is a diagrammatic cross-sectional view of a self-advancing angioscope.

The same principle of momentum transfer may be used to drive a catheter or angioscope 60, such as shown in FIG. 5, where like reference numerals are used to denote like parts. In this instance, the device 1 has a body 2 formed of a flexible tube 61 and the movable mass 3 is in the form of a plurality of balls 62, arranged to travel as a set of piston elements 4 along a channel 5. A conduit 6 opens into the channel 5 to allow for a first flow path 21 to be established, for driving the balls 62 in a forward direction, indicated by arrow "A". A return passage 46 provides for a second flow path 22 to be established, to allow fluid to escape from a region 15, between the mass 2 and a front end 13 of the body 2 as the balls 62 are driven forwardly. A third flow path 23 then allows pressurised fluid to be injected back into the region 15 to drive the mass 3 in a reverse direction. The work cycles for the device 1 of the angioscope 60 are thereby the same as those described with reference to the device of FIGS. 1 to 3.

The invention may, accordingly, be utilised in any suitable application or field such as where a remotely actuable self-advancing probe is required, either in the medical, surveillance or other relevant fields such as inspection and or maintenance of pipelines, cable and wire hoses, and search and rescue operations.

Further, it should be appreciated that many alterations and variations may be made without departing from the spirit and scope of the invention. For example, the body 2 of the device may be either rigid or flexible, as described with reference to FIG. 5. The moving mass 2 may be propelled by means of any one of gas pressure; liquid pressure; electromagnetic linear type motor or solenoid; light (photonic) pressure; sound and ultrasonic pressure; gas density gradient; or combination of any of above. The moving mass (piston) or set of moving masses (pistons) can be made of solid substance or be a column of liquid or gas moving in elongated tubular body (cylinder) with the speed function as described above with reference to the FIG. 2. The moving mass can be of any shape and form.

The device 1,40 or probe can be propelled with the energy delivered from an external source via flexible means for example—pipe, electric wire/cable, fiber optic cable and/or mechanical flexible wire etc. If the self-advancing probe (endoscope, angioscope or catheter) advances in a medium with changes in path topology such as bends, increased resistance and friction, the average cycle speed of repetitive moving mass (piston) motion has to be adjusted to ensure advancing properties. The probe can be a self containing unit with the propellant or energy source attached to the body of the probe—for example—the probe is propelled by the linear motion electromagnetic motor (solenoid, etc.)—the probe itself, control device and set of batteries can be encapsulated into one unit. The self-advancing probe (endoscope, angioscoope, catheter) may serve as a vehicle for delivery of functional devices such as sensory and surveillance devices, manipulators, containers, communication, lighting and dosing devices etc.

The invention claimed is:

1. A device which includes an elongate body with a movable mass arranged to decelerate toward an end of the body in order to impart forward movement thereto, via momentum transfer, and to accelerate away from said end in order to further drive the body forward, again using momentum transfer, wherein the device defines a first flow path for applying pressurized fluid to a rear of the moveable mass and a second flow path for allowing the fluid to be discharged from between a front of the moveable mass and the end of the body, wherein fluid flow along the second flow path is reduced as the moveable mass approaches the end of the body, in order to provide a fluid cushion to dampen impact between the moveable mass and the body and wherein a third flow path is provided to inject fluid between the moveable mass and the end of the body, in order to accelerate the moveable mass in a rearward direction relative to the end of the body, wherein the device is a self advancing probe, and wherein the self advancing probe is an endoscope.

2. A device as claimed in claim 1, wherein the mass is a piston element.

3. A device as claimed in claim 2, wherein a sensor is provided to determine the proximity of the element relative to the end of the body.

4. A device as claimed in claim 2, wherein the second flow path is provided in a conduit, which extends axially through the element and the body, and the third flow path is also through the conduit, in a reverse direction to the second flow path.

5. A device as claimed in claim 2, wherein the element slides in a channel, within the body, and a conduit extends axially through the channel and the element, for providing pressurized fluid to the device, wherein valves are arranged in the conduit to direct the pressurized fluid into a region between a rear of the body and a rear of the clement, along the first flow path, and to direct fluid from the conduit along the third flow path, into a second region, in front of the element, for driving the element in a reverse direction, and wherein the second flow path passes through openings formed in the channel and into a return passage formed in the body fluid to exit the second region along the second flow path, as the element is moved forward.

6. A device as claimed in claim 5, wherein the valves include a main valve positioned in a forward end of the conduit and secondary valves arranged adjacent the first region, wherein a positive fluid pressure is maintained in the conduit and the valve is in a closed condition when the element travels in a forward direction, so that fluid is directed through the secondary valves, into the first region between the conduit and the body, to drive the element in the forward direction.

7. A device as claimed in claim 6, wherein additional valves are provided to vent fluid captured between a rear end of the body and the element directly into the second flow path, when the element is moved rearward of the body.

8. A device as claimed in claim 1, wherein the mass includes a plurality of piston elements.

9. A device as claimed in claim 8, wherein the piston elements are in the form of balls.

10. A device, as claimed in claim 1, wherein the probe is provided with a light source and camera.

11. A device, as claimed in claim 10, wherein the probe includes location means for securing the probe relative to adjoining structure.

12. A device, as claimed in claim 1, wherein the endoscope is disposable.

13. A method of generating movement in a self-advancing device as claimed in claim 1, including rapidly decelerating the moveable mass toward an end of the body to impart forward movement thereto, via momentum transfer and accelerating the moveable mass away from said end in order to further drive the body forward, again using momentum transfer, by injecting fluid between the moveable mass and the end of the body.

14. A device which includes an elongate body with a movable mass arranged to decelerate toward an end of the body in order to impart forward movement thereto, via momentum transfer, and to accelerate away from said end in order to further drive the body forward, again using momentum transfer, wherein the device defines a first flow path for applying pressurized fluid to a rear of the moveable mass and a second flow path for allowing the fluid to be discharged from between a front of the moveable mass and the end of the body, wherein fluid flow along the second flow path is reduced as the moveable mass approaches the end of the body, in order to provide a fluid cushion to dampen impact between the moveable mass and the body and wherein a third flow path is provided to inject fluid between the moveable mass and the end of the body, in order to accelerate the moveable mass in a rearward direction relative to the end of the body, wherein the mass is a piston element, and wherein a sensor is provided to determine the proximity of the element relative to the end of the body.

15. A device which includes an elongate body with a movable mass arranged to decelerate toward an end of the body in order to impart forward movement thereto, via momentum transfer, and to accelerate away from said end in order to further drive the body forward, again using momentum transfer, wherein the device defines a first flow path for applying pressurized fluid to a rear of the moveable mass and a second flow path for allowing the fluid to be discharged from between a front of the moveable mass and the end of the body, wherein fluid flow along the second flow path is reduced as the moveable mass approaches the end of the body, in order to provide a fluid cushion to dampen impact between the moveable mass and the body and wherein a third flow path is provided to inject fluid between the moveable mass and the end of the body, in order to accelerate the moveable mass in a rearward direction relative to the end of the body, wherein the mass is a piston element, and wherein the element slides in a channel, within the body, and a conduit extends axially through the channel and the element, for providing pressurized fluid to the device, wherein valves are arranged in the conduit to direct the pressurized fluid into a region between a rear of the body and a rear of the element, along the first flow path, and to direct fluid from the conduit along the third flow path, into a second region, in front of the element, for driving the element in a reverse direction, and wherein the second flow path passes through openings formed in the channel and into a return passage formed in the body fluid to exit the second region along the second flow path, as the element is moved forward.

* * * * *

UNITED STATES PATENT AND TRADEMARK OFFICE
CERTIFICATE OF CORRECTION

| | |
|---|---|
| PATENT NO. | : 7,481,764 B2 |
| APPLICATION NO. | : 10/499426 |
| DATED | : January 27, 2009 |
| INVENTOR(S) | : Mikhail Soutorine, Nurbey Gulia and Igor Tchepikov |

It is certified that error appears in the above-identified patent and that said Letters Patent is hereby corrected as shown below:

On Column 5, Line 25, in Claim 1, change "self advancing" to --self-advancing--.

On Column 5, Line 25, in Claim 1, change "self advancing" to --self-advancing--.

On Column 5, Line 42, in Claim 5, change "clement" to --element--.

Signed and Sealed this

Thirtieth Day of June, 2009

JOHN DOLL
*Acting Director of the United States Patent and Trademark Office*